US010232064B2

(12) United States Patent
Huang

(10) Patent No.: US 10,232,064 B2
(45) Date of Patent: Mar. 19, 2019

(54) METHOD FOR STERILIZING BIOLOGICAL MATERIALS

(75) Inventor: Lynn L. H. Huang, Yongkang (TW)

(73) Assignee: National Cheng Kung University, Tainan (TW)

(*) Notice: Subject to any disclaimer, the term of this patent is extended or adjusted under 35 U.S.C. 154(b) by 676 days.

(21) Appl. No.: 13/326,391

(22) Filed: Dec. 15, 2011

(65) Prior Publication Data
US 2012/0164023 A1 Jun. 28, 2012

Related U.S. Application Data

(63) Continuation-in-part of application No. 11/866,564, filed on Oct. 3, 2007, now abandoned.

(30) Foreign Application Priority Data

Oct. 4, 2006 (TW) .............................. 95136924 A

(51) Int. Cl.
A61L 2/00 (2006.01)
A61L 2/20 (2006.01)
(52) U.S. Cl.
CPC ............. *A61L 2/0094* (2013.01); *A61L 2/202* (2013.01)
(58) Field of Classification Search
CPC .............................. A61L 2/202; A61L 2/0094
USPC .......................................................... 422/28
See application file for complete search history.

(56) References Cited

U.S. PATENT DOCUMENTS

| 4,182,663 | A | * | 1/1980 | Vaseen ...................... 204/157.3 |
| 5,460,962 | A | | 10/1995 | Kemp |
| 5,485,496 | A | | 1/1996 | Lee et al. |
| 5,700,426 | A | | 12/1997 | Schmitthaeusler et al. |
| 5,749,203 | A | * | 5/1998 | McGowan, Jr. ...... B65B 31/028 53/432 |
| 5,788,941 | A | | 8/1998 | Dalmasso et al. |
| 6,096,266 | A | | 8/2000 | Duroselle |
| 2001/0018072 | A1 | | 8/2001 | Unger |
| 2003/0031581 | A1 | | 2/2003 | Miekka et al. |
| 2003/0058982 | A1 | * | 3/2003 | Nagase et al. ................ 376/310 |
| 2004/0022666 | A1 | | 2/2004 | Biddle et al. |

FOREIGN PATENT DOCUMENTS

| CN | 1427729 | 7/2003 |
| TW | 061995 | 10/1984 |
| TW | 115972 | 7/1989 |
| TW | 149465 | 3/1990 |

(Continued)

OTHER PUBLICATIONS

English language translation of abstract of TW 115972.

(Continued)

*Primary Examiner* — Kevin Joyner
(74) *Attorney, Agent, or Firm* — Cesari and McKenna, LLP

(57) ABSTRACT

A method for sterilizing biological materials is disclosed. After dehydrating the biological material, the dehydrated biological material is put into a closed container, and 0.01 g/m$^3$ to 1000 g/m$^3$ or an enough dose of ozone gas is introduced into the container for a period of time until the biological material is completely sterilized. Afterward, the ozone gas is removed from the closed container to finish sterilization of the biological material.

9 Claims, 3 Drawing Sheets

(56) References Cited

FOREIGN PATENT DOCUMENTS

| | | |
|---|---|---|
| TW | 145942 | 11/1990 |
| TW | 241193 | 2/1995 |
| TW | 310308 | 7/1997 |
| TW | 443932 | 7/2001 |
| TW | 474828 | 2/2002 |
| TW | 512064 | 12/2002 |
| WO | WO 0170279 | 9/2001 |

OTHER PUBLICATIONS

English language translation of abstract of TW 474828.
English language translation of abstract of TW 310308.
English language translation of abstract of TW 241193.
English language translation of abstract of TW 149465.
English language translation of abstract of TW 443932.
English language translation of abstract of TW 061995.
English language translation of abstract of TW 512064.
English language translation of abstract of CN 1427729.

\* cited by examiner

METHOD FOR STERILIZING BIOLOGICAL MATERIALS

CROSS REFERENCE TO RELATED APPLICATION

This application is a continuation-in-part of U.S. application Ser. No. 11/866,564 filed on Oct. 3, 2007, and claims priority under 35 U.S.C. § 119(e) to Taiwan Application Serial Number 095136924 filed on Oct. 4, 2006, the entire contents of which are incorporated by reference herein.

BACKGROUND OF THE INVENTION

1. Field of the Invention

The present invention relates to a sterilizing method. More particularly, the present invention relates to a method for sterilizing biological materials employing ozone.

2. Description of Related Art

Typically, biological materials, which may refer to materials existing in or derived from living organisms, substantially comprise components, such as amino acids, peptides, proteins, polysaccharides and so on, directly extracted from microorganisms, animals or plants. As the biological material itself possesses excellent biocompatibility, it has potential in medical applications, for example, wound dressing and scaffold for tissue engineering, as well as in pharmaceutical and cosmetic industries. The biological materials for human or living organisms must be subjected to a strictly sterilizing procedure. However, most of the biological materials are susceptible to high temperature sterilization, and they are also liable to be denatured. The option of methods for sterilizing the biological materials is very restricted. Thus, the application of the biological materials is presently focused on how to achieve the sterilizing effect and to save the bioactivity of biological materials, rather than destroying their properties.

There are several methods of sterilizing biological materials as follows. (1) Sterilization with 75% ethanol: The biological material is immersed in 75% ethanol, and it must be reserved and delivered in moist state. However, the bioactive components are liable to be denatured in such moist state. Moreover, it is not sure whether ethanol is completely removed from or remains in the biological material when rinsing it before use. (2) Sterilization with gamma (γ)-irradiation as disclosed in U.S. Pat. No. 5,485,496, and Taiwan Pat. Nos. 145,942 and 115,972: This method is applied commonly, which employs γ-ray to irradiate the biological materials. However, the energy of the γ-ray is so high that some chemical structures of the biological material are destroyed, resulting in weakening the mechanical strength of the biological material. In addition, the irradiation is hazardous to human so that it has to be operated in a specific place, resulting in inconvenient usage. (3) Sterilization with ultraviolet light as disclosed in Taiwan Pat. No. 474,828: This method employs ultraviolet light to irradiate the biological materials for sterilization. Nevertheless, the ultraviolet light penetrates to minimal distances and only the surfaces of the biological materials can be sterilized. Thus, the ultraviolet light is unavailable to sterilize the biological materials mostly with three-dimensional shape and opaque property. (4) Sterilization with chemical reagents as disclosed in U.S. Pat. Nos. 5,460,962 and 6,096,266, as well as Taiwan Pat. Nos. 310,308, 241,193 and 149,465: This method is accomplished by adding chemical bactericides into the biological materials. However, the chemical bactericides are toxic and difficult to be removed, so it is applied in fewer fields. (5) Sterilization with high temperature and high pressure (autoclave) as disclosed in Taiwan Pat. No. 443,932: The autoclave method results in the denaturation of biological materials, even completely losing their bioactivity. In sum, the aforementioned methods have respective drawbacks, which often cause biological materials to change in chemical structures and properties, resulting in biocompatibility and applicability.

Ozone is typically applied in surface modification of polymeric biomaterials. Ozonization refers to generate activated peroxide on the surface of the biomaterial, and it further induces graft copolymerization with some functional groups on the biomaterial, as well as degradation in aqueous environment. For the use of sterilization, ozone is usually applied in sterilization of general instruments as disclosed in U.S. Pat. No. 5,788,941 and Taiwan Pat. No. 061,995. This method is accomplished by placing the object into an ozone-containing environment. In general, a biological material has certain aqueous content and even exists in a solution state. As such for the aqueous biological material, the aqueous content existing in the sample may react with ozone gas, resulting in changes of chemical functional groups inside the biological material, and even microchanges inside the structures of the biological material, such as polymerization, degradation and so on, thereby affecting physiochemical properties of the biological material. On the other hand, as such for the biological material in solution state, ozone dissolved in the solution may be insufficient to achieve a desirable sterilizing effect. If ozone is directly introduced into an aqueous solution, the same problem caused by ozone sterilization to the water-containing biological material will happen.

For the foregoing reasons, it is necessary to develop a method for sterilizing biological materials, while maintaining bioactivity and structure thereof, such that the method can be widely applied to the biological materials.

SUMMARY OF THE INVENTION

The present invention develops a novel method for sterilizing biological materials, which can overcome the shortcoming of the biological materials that those structures can be destroyed by ozone in the prior art, and further apply ozone to sterilize the biological materials.

According to one embodiment of the present invention, a method for sterilizing biological materials is provided as follows. After dehydrating the biological material, the dehydrated biological material is put into a closed container, and 0.01 g/m$^3$ to 1000 g/m$^3$ or an enough dose of pure ozone gas is introduced into the container for a period of time until the biological material is completely sterilized. Afterward, the ozone gas is removed from the closed container to finish sterilization of the biological material. During the sterilization, the other gases are not introduced into the container.

According to another embodiment of the present invention, a method for sterilizing collagen is provided as follows. After dehydrating the collagen, the dehydrated collagen is put into a closed container, and 0.01 g/m$^3$ to 1000 g/m$^3$ of pure ozone gas is introduced into the container for a period of time until the collagen is completely sterilized. Afterward, the ozone gas is removed from the closed container to finish sterilization of the collagen. During the sterilization, the other gases are not introduced into the container.

BRIEF DESCRIPTION OF THE DRAWINGS

The foregoing aspects and many of the attendant advantages of this invention are more readily appreciated and better understood by referencing the following detailed description, when taken in conjunction with the accompanying drawings, wherein.

DETAILED DESCRIPTION OF THE PREFERRED EMBODIMENT

Figure 1:
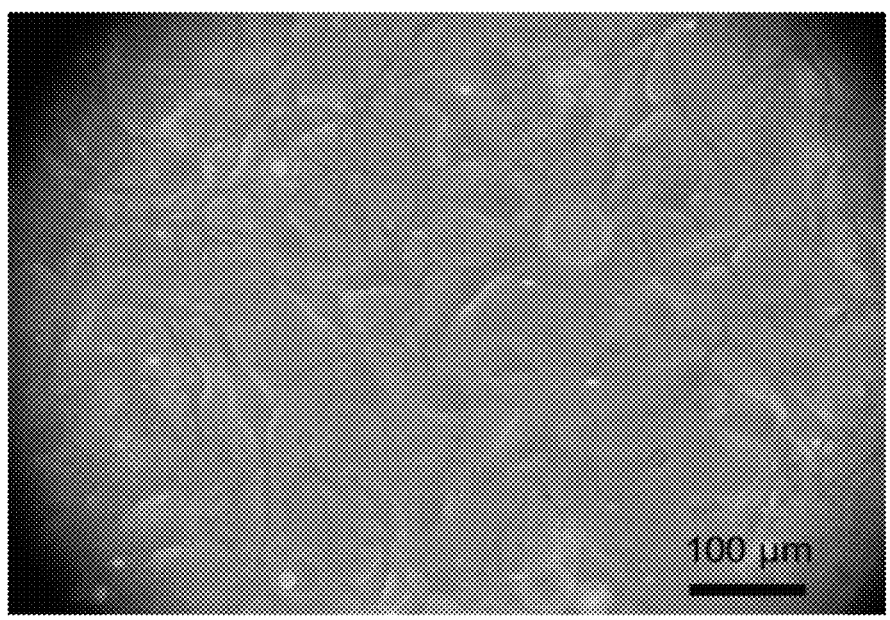
FIG. 1 is a micrograph at 100 times of magnification showing fibroblast morphology according to an embodiment of the present invention, where the fibroblasts were cultured on the collagen matrix sterilized by the present method.

The below description providing various embodiments and specific details of the invention is illustrative only and should not be construed in any way as limiting the invention. Furthermore, various applications of the invention, and modifications thereto, which may occur to those who are skilled in the art, are also encompassed by the general concepts described below.

The present invention provides a method for sterilizing biological materials. In one embodiment, the method for sterilizing biological materials is performed as follows. After dehydrating the biological material, the dehydrated biological material is put into a closed container, and 0.01 $g/m^3$ to 1000 $g/m^3$ or an enough dose of ozone gas is introduced into the container for a period of time until the biological material is completely sterilized. Afterward, the ozone gas is removed from the closed container to finish sterilization of the biological material.

"An enough dose" means a does of ozone gas that is able to achieve complete sterilization of the biological material and can be changed according to the concentration of the biological material and the volume of the closed container. "The biological material" in the specification refers to a material existing in a living organism, produced by a living organism or for use in a living organism. A preferred embodiment of the biological material of the present invention is a material, for example, growth factor, antibody, hormone, protein drug, collagen, gelatin, lipid, fat, ribonucleotides, deoxyribonucleotides, ribonucleic acids, deoxyribonucleic acids, saccharide, oligosaccharide, polysaccharide, hyaluronan, elastin, chondroitin sulfate, heparin, heparin sulfate, dermatan sulfate, glycosaminoglycan, chitin, chitosan, alginate or related derivatives, existing in a living organism. However, collagen is more preferable among those. Moreover, the biological material of the present invention may be also a material, for example, including an enzyme, a protein product, a protein drug, a cell culture material with a biological component, an extracellular matrix, a matrix for medical use, artificial tissue and organ, a genetic-engineering product, a material of Chinese herb medicine, a product of Chinese herb medicine, a cosmetic product and a cosmetic additive, produced by a living organism. Furthermore, the biological material of the present invention may be a material, for example, including a cell culture material with a biological component, an extracellular matrix, and a matrix for medical use, artificial tissue and organ, for use in a living organism.

The present invention is characterized by removing the water from the biological material, so as to prevent the shortcomings in the prior art, such as undesired reaction between ozone and water, or the insufficient content of ozone in the water. Even though one skilled in the art commonly knows the methods and conditions how to remove the water, the present method can remove water, rather than substantially affect inherent bioactivities and physiochemical properties of the biological materials. According to an embodiment of the present invention, the aforementioned step of dehydrating the biological materials may utilize lyophilization. According to another embodiment of the present invention, the aforementioned step of dehydrating the biological materials may dry under low temperature and decreased pressure.

According to the present method, the dehydrated biological material is put into a closed container for sterilization with ozone. The closed container of the present invention is suitable for receiving the biological material therein, and it is beneficial to supply ozone gas therein or exhaust ozone gas therefrom. Preferably, the closed container has a channel for supplying and exhausting ozone, so as to control ozone in and out.

The concentration of ozone depends on the quantity and property of the biological material. In general, the ozone concentration is in a range from 0.01 $g/m^3$ to 1000 $g/m^3$ or an enough dose, and preferably, from 1 $g/m^3$ to 50 $g/m^3$. The period of sterilization time of ozone also depends on the quantity and property of the biological material until the biological material is completely sterilized. For example, 30 minutes may be needed for sterilizing the biological material of collagen.

According to the present method, the ozone gas is then removed from the closed container. One skilled in the art commonly knows the methods how to remove the ozone gas. In a preferred embodiment of the present invention, the ozone gas may be removed in the manner of vacuuming removal, sterile gas exchange removal or standing removal.

According to the present method, after dehydrating the biological material, the chemical structure of the dehydrated biological material sterilized by ozone is destroyed far less than that sterilized by gamma (γ)-irradiation, and the biological material is neither degraded nor polymerized. Moreover, the biological material sterilized by ozone is safer than that sterilized by radioactive rays, and the ozone sterilization is conveniently applied anywhere rather than in specific place. As such, it is not worried about any irritant substance remaining in the biological material in comparison to that treated by chemical cross-linking agents. Besides, the ozone sterilization is beneficial to retain inherent properties of biological materials, to preserve and to transport biological materials conveniently.

The present invention further provides another method for sterilizing collagen. In one embodiment, the method for sterilizing collagen is performed as follows. After dehydrating collagen, the dehydrated collagen is put into a closed container, and 0.01 $g/m^3$ to 1000 $g/m^3$ or an enough dose of ozone gas is introduced into the container for a period of time until the collagen is completely sterilized. Afterward, the ozone gas is removed from the closed container to finish sterilization of the collagen.

The following embodiments of the present invention are described in detail as an illustration of the present invention rather than a limitation thereof.

Example 1 Sterilization of Collagen

EXAMPLE 1 is described with respect to sterilization of the collagen solution. The collagen solution is lyophilized to dehydrate collagen molecules. And then, the dehydrated collagen is put into a closed container of 21 cm (length)×15 cm (width)×7 cm (height), and 120 mg/hour (approximately 27.2 g/m$^3$) of pure ozone gas is introduced into the container for approximate 30 minutes. Before the introduction of pure ozone, the container can be decompressed in a vacuum. The ozone gas remained in the collagen is then removed by standing at ventilated laminar flow stage for about 1 hour at room temperature, or alternatively, vacuuming for 1 hour, so as to finish sterilization of the biological material. During the sterilization, except pure ozone, the other gases are not introduced in the container.

Example 2 Effect of Ozone Sterilization of Collagen

EXAMPLE 2 is described with respect to sterilization effect on the collagen sterilized by EXAMPLE 1 as experiment, compared with that sterilized by conventionally ultra-high-speed centrifugation as comparison and/or that without sterilization as control.

Cell morphology: The human foreskin fibroblasts were seeded on the collagen matrices, which were sterilized by EXAMPLE 1 or conventional ultra-high-speed centrifugation, respectively, and their cell morphologies were observed under light microscope and photographed under 100× magnification as shown in FIG. 1. Reference is made to FIG. 1, where the fibroblasts grown on the collagen matrix sterilized by ozone gas are similar to those grown on the collagen matrix sterilized by conventionally ultra-high-speed centrifugation (not shown).

Total cell numbers: The human foreskin fibroblasts were seeded on either the collagen matrix or with collagen solution sterilized by EXAMPLE 1 or conventional centrifugation, respectively. Dulbecco's Modified Eagle's Medium (DMEM) supplemented with 10 vol. % fetal bovine serum (FBS) was used to culture fibroblasts. After a period of incubation, the collagen matrix was digested by collagenase, and the total cell numbers were then counted and the percentages of cell numbers in comparison to the control were listed as the following Table 1.

TABLE 1

| Treatment of Collagen | Total Cell Number (%) |
| --- | --- |
| Collagen solution sterilized by conventional centrifugation | 100 ± 4.3 |
| Collagen solution sterilized by ozone gas | 96 ± 4.3 |
| Collagen matrix sterilized by conventional centrifugation | 100 ± 3.4 |
| Collagen matrix sterilized by ozone gas | 106 ± 8.6 |

The result indicates that the growth of fibroblasts cultured either on the collagen matrix or with collagen solution, sterilized by EXAMPLE 1 or conventional centrifugation, was very similar.

Integrity of collagen molecule: The molecular integrity of collagen, which were collagen solution or the dehydrated collagen matrix, unsterilized or sterilized by EXAMPLE 1 or conventional centrifugation, was observed in an equivalent amount.

After sterilization, the collagen solution sterilized by ozone gas is more viscous, indicating that the ozone sterilization causes some molecular polymerization in high water content; however, the ozone sterilization causes no structural change on the dehydrated collagen matrix. Thus, it can be seen that the dehydrating step is a key step of the present method.

Sterilizing ability: The collagen solution or the dehydrated collagen matrix, either unsterilized or sterilized by EXAMPLE 1, is mixed with Staphylococcus aureus (ATCC-25178) in Luria-Bertani (LB) broth. After culturing for 16 hours, the turbidity of the cultures was monitored at 600 nm (OD600).

Figure 2:
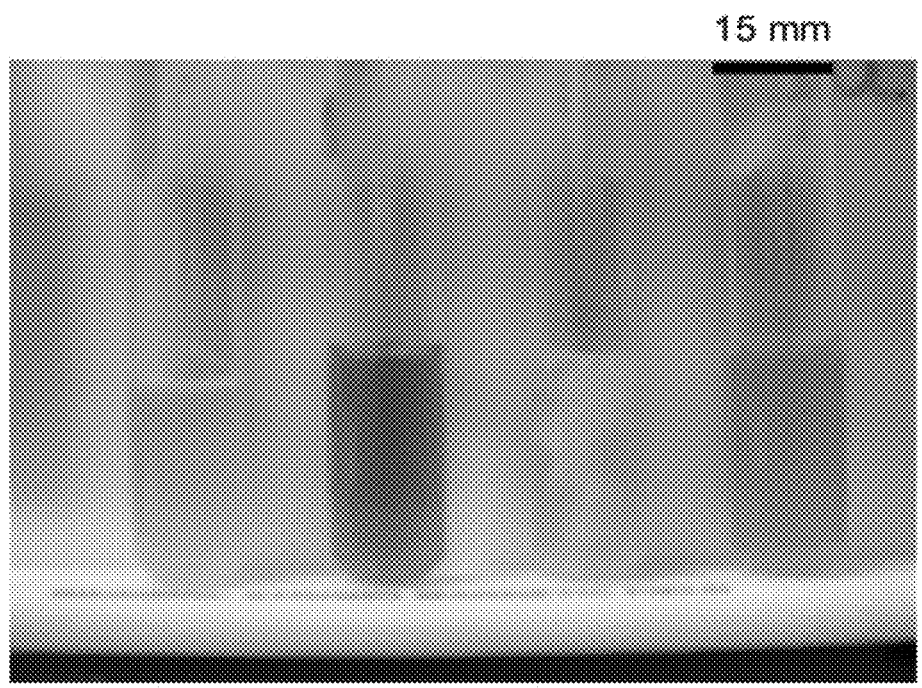
FIG. 2 is a photo of culture tubes wherein staphylococci were cultured in LB broth added with the unsterilized collagen matrix, the ozone sterilized collagen matrix, unsterilized collagen solution, and the ozone sterilized collagen solution, from left to right; after 16-hour incubation, those cultures were observed in turbidity.

Reference is made to FIG. 2, which is a photo of culture tubes wherein Staphylococcus aureus was cultured in LB broth added with the unsterilized collagen matrix, the ozone sterilized collagen matrix, unsterilized collagen solution, and the ozone sterilized collagen solution, from left to right. It can be seen that the culture incubated with unsterilized collagen matrix or solution was turbid due to staphylococci growth; however, the culture incubated with ozone sterilized collagen matrix or solution was clear. The detailed OD600 data are shown in Tab. 2. As shown in Table 2, the higher OD correlates with more staphylococci growth, so the ozone sterilization can achieve more successful sterilizing effect of the dehydrated collagen matrix than that of the collagen solution. On the contrary, the collagen unsterilized by ozone gas can enhance staphylococci grown therein. That proves the sterilizing effect of the present invention.

TABLE 2

| | | OD600 |
| --- | --- | --- |
| Dehydrated collagen matrix | Unsterilization | 1.1886 |
| | Ozone sterilization | 0.0710 |
| Collagen solution | Unsterilization | 2.0302 |
| | Ozone sterilization | 0.6288 |

Molecular Property of Sterilized Collagen: The equivalent amount of dehydrated collagen is subjected to the following respective treatments: (1) non-treatment; (2) treatment with ozone gas as EXAMPLE 1; (3) treatment with ultraviolet irradiation for 12 hours; (4) immersion in 75 vol. % ethanol for 4 hours; (5) immersion in 2 vol. % formaldehyde for 1 hour; or (6) autoclave sterilization under conventional high-temperature and high-pressure. Afterward, the respective sample from the aforementioned treatments dissolved in acetate solution, and it was then analyzed by 5% acrylamide gel electrophoresis and stained with Coomassie blue to analyze its change in components. This result is shown in FIG. 3.

Figure 3:
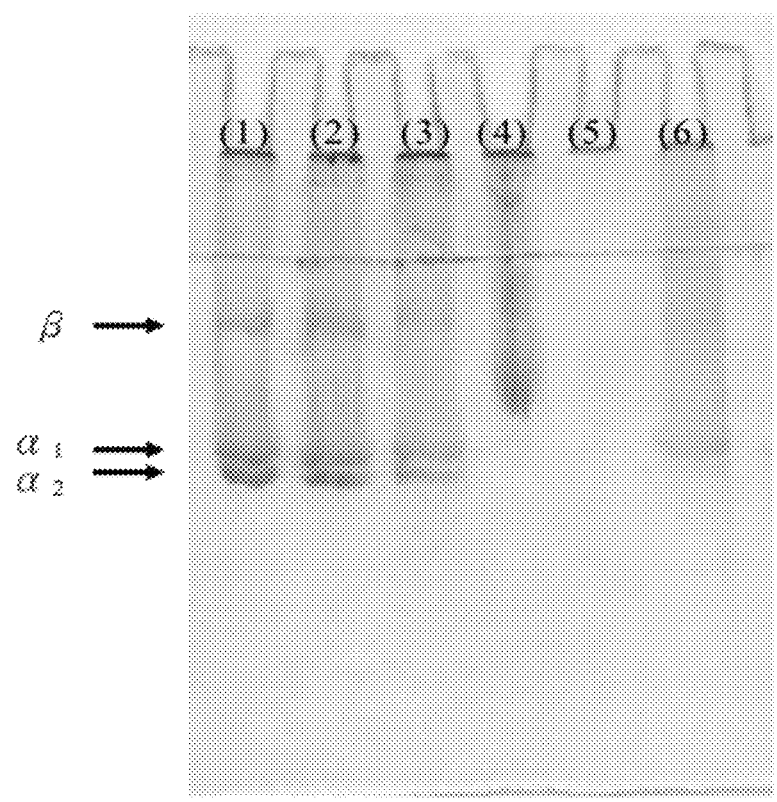
FIG. 3 is a stained electrophoresis gel of collagen subjected to the following respective treatments: (1) untreatment; (2) treatment with ozone gas as EXAMPLE 1; (3) treatment with ultraviolet irradiation for 12 hours; (4) immersion in 75 vol. % ethanol for 4 hours; (5) immersion in 2 vol. % formaldehyde for 1 hour; or (6) autoclave sterilization under conventional high-temperature and high-pressure.

Reference is made to FIG. 3. It can be seen that the dehydrated collagen treated by ozone gas [lane (2)] has biochemical components substantially the same as the control [lane (1)] and the molecular property does not be changed; the collagen treated by ultraviolet irradiation [lane (3)] has partial biochemical components to be polymerized and cleaved, and the bands of the major α1, α2 and β chains are decreased as arrowed stained density; the collagen treated by immersion in ethanol [lane (4)] reveals vague bands in the electrophoresis gel since its components are polymerized to be less soluble; the collagen treated by immersion in formaldehyde [lane (5)] reveals no band in electrophoresis gel since its components are highly polymerized to be insoluble, resulting that those polymerized components cannot be separated in the electrophoresis gel and they are lost; the collagen treated by autoclave sterilization under conventional high-temperature and high-pressure [lane (6)] is mostly degraded, exhibiting that the major bands are decreased in stained density and vague in the electrophoresis gel. It can be apparently seen that the ozone sterilization of the present method for use in collagen is better than other methods.

As is understood by a person skilled in the art, the foregoing descriptions of the embodiments of the present invention are an illustration of the present invention rather than a limitation thereof. Various modifications and similar arrangements are included within the spirit and scope of the appended claims. The scope of the claims should be accorded to the broadest interpretation so as to encompass all such modifications and similar structures. While an embodiment of the invention has been illustrated and described, it will be appreciated that various changes can be made therein without departing from the spirit and scope of the invention.

What is claimed is:

1. A method for sterilizing a biological material, comprising:
    dehydrating a biological material, wherein the biological material is selected from the group consisting of a collagen and related derivatives thereof;
    putting the dehydrated biological material into a closed container, decompressing the closed container under a vacuum, and introducing 0.01 g/m$^3$ to about 1000 g/m$^3$ of ozone gas, without introducing any other gases, into the closed container in the absence of water for a period of time until the dehydrated biological material is completely sterilized; and
    removing the ozone gas from the closed container by utilizing vacuum degassing or standing degassing to finish sterilization of the dehydrated biological material, wherein the dehydrated biological material substantially remain intact after having been subjected to the sterilization, and the dehydrated biological material is applied in medical, pharmaceutical, or cosmetic industries.

2. The method of claim 1, wherein the biological material is a material produced by a living organism.

3. The method of claim 1, wherein the biological material is a material for use in a living organism.

4. The method of claim 1, wherein the step of dehydrating the biological material is carried out by lyophilization.

5. The method of claim 1, wherein the step of dehydrating the biological material is carried out by drying under decreased pressure.

6. A method for sterilizing collagen, comprising:
    dehydrating collagen;
    putting the dehydrated collagen into a closed container, decompressing the closed container under a vacuum, and introducing 0.01 g/m$^3$ to about 1000 g/m$^3$ of ozone gas, without introducing any other gases, into the closed container in the absence of water for a period of time until the dehydrated collagen is completely sterilized; and
    removing the ozone gas from the closed container by utilizing vacuum degassing or standing degassing to finish sterilization of the dehydrated biological material, wherein the dehydrated collagen substantially remain intact after having been subjected to the sterilization, and the dehydrated collagen is applied in medical, pharmaceutical, or cosmetic industries.

7. The method of claim 6, wherein the step of dehydrating the collagen is carried out by lyophilization.

8. The method of claim 6, wherein the step of dehydrating the collagen is carried out by drying under low temperature and decreased pressure.

9. A method for sterilizing a dehydrated biological matrix, comprising:
    putting a dehydrated biological matrix into a closed container, decompressing the closed container under a vacuum, and introducing 0.01 g/m$^3$ to about 1000 g/m$^3$ of ozone gas, without introducing any other gases, into the closed container in the absence of water for a period of time until the dehydrated biological matrix is completely sterilized, wherein the dehydrated biological matrix is collagen, gelatin, or related derivatives thereof; and
    removing the ozone gas from the closed container by utilizing vacuum degassing or standing degassing to finish sterilization of the dehydrated biological material, wherein the dehydrated biological matrix substantially remain intact after having been subjected to the sterilization, and the dehydrated biological matrix is applied in medical, pharmaceutical, or cosmetic industries.

* * * * *